United States Patent [19]

Smith et al.

[11] Patent Number: 5,792,838
[45] Date of Patent: Aug. 11, 1998

[54] METHOD FOR STABILIZING IMMUNOGLOBULIN COMPOSITIONS

[75] Inventors: Marjorie Smith; Valentina Riveros-Rojas, both of Beckenham, Great Britain

[73] Assignee: Glaxo Wellcome Inc., Research Triangle Park, N.C.

[21] Appl. No.: 465,319

[22] Filed: Jun. 5, 1995

Related U.S. Application Data

[63] Continuation of Ser. No. 232,127, Apr. 28, 1994.

[30] Foreign Application Priority Data

Oct. 28, 1991 [GB] United Kingdom ............... 9122820

[51] Int. Cl.$^6$ ................................................. C07K 16/00
[52] U.S. Cl. ................... 530/387.1; 530/387.3; 530/388.1; 530/389.1
[58] Field of Search ................. 530/387.1, 388.1, 530/389.1, 387.3

[56] References Cited

U.S. PATENT DOCUMENTS

| | | |
|---|---|---|
| 2,149,304 | 3/1939 | Masucci . |
| 4,722,899 | 2/1988 | Hamaoka et al. .............. 435/172.2 |
| 5,087,695 | 2/1992 | McAuley ....................... 530/412 |
| 5,367,060 | 11/1994 | Vandlen et al. ................ 530/399 |

FOREIGN PATENT DOCUMENTS

| | | |
|---|---|---|
| 0391526 | 10/1990 | European Pat. Off. . |
| 0481790 | 4/1992 | European Pat. Off. . |
| 531539 | 3/1993 | European Pat. Off. . |
| 9109967 | 7/1991 | WIPO . |

OTHER PUBLICATIONS

Velander et al., Biotechnology Progress, vol. 5, No. 3, pp. 119–125, (1989).
Chvapil et al., Biochemical Pharmacology, vol. 21, pp. 1097–1105, 1972.
Borrebaeck, Journal of Immunological Methods, vol. 123, pp. 157–165 (1989).
Harris et al., TIBTECH, vol. 11, pp. 42–44, (1993).
Bach et al., Immunology Today, vol. 14, No. 9, pp. 421–425, (1993).
Waldmann, Science, vol. 252, pp. 1657–1662, (1991).
Seaver, Genetic Engineering News, pp. 10 and 21 (1994).
Osband et al., Immunology Today, vol. 11, No. 6, pp. 193–195 (1990).
Baker et al., Biol. Chem., vol. 253, pp. 844–845, (1978).
Riechmann et al., Nature, vol. 332, pp. 323–327 (1988).

*Primary Examiner*—Frank C. Eisenschenk
*Attorney, Agent, or Firm*—Nixon & Vanderhye P.C.

[57] ABSTRACT

The invention relates to a stabilised immunoglobulin composition comprising at least one immunoglobulin together with a stabilising amount of a chelator of copper ions such as EDTA or citrate. Preferably the immunoglobulin is an antibody, for example a recombinant CDR-grafted antibody against the CDw52 antigen, most preferably CAMPATH-1H. The invention also relates to a process for enhancing the stability of an immunoglobulin which comprises subjecting the immunoglobulin to a purification procedure capable of removing copper ions therefrom. Preferably the immunoglobulin is rendered substantially free from detectable copper ions, for example on atomic absorption spectroscopy.

5 Claims, No Drawings

METHOD FOR STABILIZING IMMUNOGLOBULIN COMPOSITIONS

This is a continuation of application Ser. No. 08/232,127 filed Apr. 28, 1994.

STABILISED ANTIBODIES

The present invention relates to the stabilisation of immunoglobulins against degradation, in particular on storage and processing prior to use.

Antibodies or immunoglobulins are proteinaceous bifunctional molecules. One part, which is highly variable between different antibodies, is responsible for binding to an antigen, for example the many different infectious agents that the body may encounter, whilst the second, constant, part is responsible for binding to the Fc receptors of cells and also activates complement. In this way, antibodies represent a vital component of the immune response of mammals in destroying foreign microorganisms and viruses.

The immunisation of an animal with an antigen results in the production of different antibodies with different specificities and affinities. An antiserum obtained from the immunised animal will, therefore, be heterogeneous and contain a pool of antibodies produced by many different lymphocyte clones. Antibodies thus obtained are referred to as polyclonal antibodies and this polyclonal nature has been a major drawback in the use of antibodies in diagnostic assays and in therapeutic applications.

A major step forward occurred in 1975 when Kohler and Milstein (Nature, 1975, 256, 495–497) reported the successful fusion of spleen cells from mice immunized with an antigen with cells of a murine myeloma line. The resulting hybrid cells, termed hybridomas, have the properties of antibody production derived from spleen cells and of continuous growth derived from the myeloma cells. Each hybridoma synthesizes and secretes a single antibody to a particular determinant of the original antigen. To ensure that all cells in a culture are identical, i.e. that they contain the genetic information required for the synthesis of a unique antibody species, the hybridomas resulting from cell fusion are cloned and subcloned. In this way, the cloned hybridomas produce homogeneous or monoclonal antibodies.

The advantages of hybridoma technology are profound. Because many hybrids arising from each spleen are screened for their potential to produce antibodies to the antigen of interest and only a few are selected, it is possible to immunize with impure antigens and yet obtain specific antibodies. The immortality of the cell line assures that an unlimited supply of a homogeneous, well-characterised antibody is available for use in a variety of applications including in particular diagnosis and immunotherapy of pathological disorders. Unfortunately, the usefulness of such monoclonal antibodies in a clinical setting can be severely hampered by the development of human anti-mouse antibodies—an anti-globulin response—which may interfere with therapy or cause allergic or immune complex hypersensitivity. This has led to the development of humanised antibodies.

An antibody molecule is composed of two light chains and two heavy chains that are held together by interchain disulphide bonds. Each light chain is linked to a heavy chain by disulphide bonds and the two heavy chains are linked to each other by disulphide bonds. Each heavy chain has at one end a variable domain followed by a number of constant domains, and each light chain has a variable domain at one end and a constant domain at the other end. The light chain variable domain is aligned with the variable domain of the heavy chain. The light chain constant domain is aligned with the first constant domain of the heavy chain. The remaining constant domains of the heavy chains are aligned with each other. The constant domains in the light and heavy chains are not involved directly in binding the antibody to the antigen.

The variable domains of each pair of light and heavy chains form the antigen binding site. They have the same general structure with each domain comprising a framework of four regions, whose sequences are relatively conserved, connected by three complementarity determining regions (CDRs). The four framework regions largely adopt a beta-sheet conformation and the CDRs form loops connecting, and in some cases comprising part of, the beta-sheet structure. The CDRs are held in close proximity by the framework regions and, with the CDRs from the other domain, contribute to the formation of the antigen binding site.

In the use of murine monoclonal antibodies, the induction of an human anti-mouse antibody response is due to the murine origin of the constant domains and four framework regions. This problem has therefore been addressed by the development of modified antibodies of two basic types. The first type, referred to as chimeric antibodies, is where the murine constant domains only are replaced by equivalent domains of human origin (Morrison et al. P.N.A.S., 1984, 81, 6851–6855; Boulianne et al, Nature, 1985, 314, 268–270; and Neuberger et al, Nature, 1985, 314, 268–270). The second type is where the murine constant domains and the murine framework regions are all replaced by equivalent domains and regions of human origin. This second type of modified antibody is referred to as a humanised or CDR-grafted antibody (Jones et al, Nature, 1986, 321, 522–525; and Riechmann et al, Nature, 1988, 332, 323–327).

To generate sufficient quantities of antibody for full clinical investigation, it is desirable to utilize an efficient recombinant expression system. Since myeloma cells represent a natural host specialized for antibody production and secretion, cell lines derived from these have been used for the expression of recombinant antibodies. Often, complex vector design, based around immunoglobulin gene regulatory elements, is required, and final expression levels have been reported which are highly variable (Winter et al, Nature, 1988, 332, 323–327; Weidle et al, Gene, 1987, 60, 205–216; Nakatani et al, Bio/Technology, 1989, 7, 805–810; and Gillies et al, Bio/Technology, 1989, 7, 799–804).

Other types of expression systems which have been proposed for antibodies include immortalised human B cells (Rice et al, Proc. Natl. Acad. Sci. USA, (1982) 79 7862–7865), however yields are generally low and it is difficult to establish stable cell lines. E. coli has been used to express $F_v$ fragments (Skerra & Plukthun, Science, (1988) 240, 1038–1041) or single chain antigen binding molecules (Bird et al, Science, (1988) 242, 423–426) but entire immunoglobulins have so far not been produced in the system. Antibodies have, however, been successfully produced in mammalian cell expression systems which are already known for the production of recombinant proteins such as Chinese hamster ovary (CHO) cells.

In the production of purified antibodies whether for therapeutic or diagnostic use, it is important that the antibody is sufficiently stable on storage and various chemical entities may have an adverse effect on the stability of the antibody. The present invention is based on the surprising discovery that trace amounts of copper ($Cu^{++}$) have a destabilising effect on immunoglobulin molecules on storage and that this effect can be eliminated by formulating the immunoglobulin molecule with a suitable chelator of copper ions.

It has also surprisingly been found that the presence of a chelator of copper ions may have a stabilising effect on the immunoglobulin molecule even when the immunoglobulin does not contain amounts of copper which are detectable by conventional techniques such as atomic absorption spectroscopy. Whilst not wishing to be bound by any particular theory, it may be that the presence of copper ions in amounts below the detection limits of techniques such as atomic absorption spectroscopy still has a destabilising effect on the immunoglobulin molecule which can be eliminated by the addition of a suitable chelating agent.

The present invention provides a stabilised immunoglobulin composition comprising at least one immunoglobulin together with a stabilising amount of a chelator of copper ions.

The invention also provides the use of a chelator of copper ions to stabilise an immunoglobulin against degradation on storage, for example degradation resulting from the effect of copper ions.

The fact that trace amounts of copper ions have a destabilising effect on immunoglobulins means that there may be an advantage in terms of stability in ensuring that immunoglobulins contain the minimum possible amount of copper ions. According to a further aspect the present invention provides a purified immunoglobulin substantially free from copper ions. In particular the invention provides an immunoglobulin in which no copper can be detected by the use of conventional techniques such as atomic absorption spectroscopy.

The invention also provides a process for enhancing the stability of an immunoglobulin which comprises subjecting the immunoglobulin to a purification procedure capable of removing copper ions therefrom. In particular the procedure should be such that the no copper can be detected in the immunoglobulin by the use of conventional procedures such as atomic absorption spectroscopy. Copper can be removed from immunoglobulins by conventional procedures known in the field of protein purification such as dialysis versus potassium cyanide containing phosphate buffer followed by gel filtration to remove copper as copper cyanide (see for example Baker and Hultquist, J. Biol. Chem., 253, 844–845 (1978)).

The present invention is applicable to the stabilization of immunoglobulins of all classes, i.e IgM, IgG, IgA, IgE and IgD, and it also extends to the stabilisation of Fab fragments and bispecific antibodies. The invention is preferably applied to the stabilisation of immunoglobulins of the class IgG, which includes the sub-classes $IgG_1$, $IgG_{2A}$, $IgG_{2B}$, $IgG_3$ and $IgG_4$. The invention is more preferably applied to the stabilisation of immunoglobulins of the class $IgG_1$.

The invention finds particular application in the stabilisation of recombinant antibodies, most particularly chimeric antibodies or humanised (CDR-grafted) antibodies. Particular examples of these include chimeric or humanised antibodies against CD2, CD3, CD4, CD5, CD7, CD8, CD11a,b, CD18, CD19, CD25, CD33, CD54 and especially humanised antibodies against the CDw52 antigen, such as CAMPATH-1H (CAMPATH is a Trade Mark of the Wellcome group of companies). Further examples include chimeric or humanised antibodies against various tumour cell marker antigens.

The immunoglobulin will generally be formulated with the metal ion chelating agent at an early stage, for example during or immediately following purification. The production procedure for an immunoglobulin will generally involve purification by means of chromatography and/or gel filtration columns. The chelating agent can be added at any convenient stage of the purification procedure, for example at the stage of the final column, so that the chelating agent remains in the immunoglobulin at the end of the purification procedure. Alternatively, the chelating agent may be added at a suitable stage following purification. In the case of a lyophilised immunoglobulin the chelating agent will generally be added prior to lyophilisation.

The level at which the chelating agent is added to the immunoglobulin will be such as to ensure that any copper present is bound by the chelating agent and thus rendered ineffective in destabilising the immunoglobulin. The invention is applicable irrespective of the intended end use of the immunoglobulin although the chelating agent which is used should be chosen in such a way that it will not have an adverse effect on the intended end use of the immunoglobulin. For example in the case of antibodies intended for therapeutic use, the chelating agent should not show any toxic effects at the level in which it will be present.

A particularly preferred metal ion chelating agent is ethylenediamine tetraacetic acid (EDTA) which may typically be added to the immunoglobulin at levels of 0.05 mM to 5 mM, preferably 0.1 mM to 3 mM. A level of 0.1 mM EDTA will often be sufficient to stabilise an immunoglobulin but levels up to 2 mM or higher do not present any problem physiologically in the case of an immunoglobulin intended for administration to humans. An alternative metal ion chelating agent is citrate ion, preferably used in the form of an alkali metal citrate, e.g. sodium citrate.

Immunoglobulins intended for therapeutic use will generally be administered to the patient in the form of a pharmaceutical formulation. Such formulations preferably include, in addition to the immunoglobulin, a physiologically acceptable carrier or diluent, possibly in admixture with one or more other agents such as other immunoglobulins or drugs, such as an antibiotic. Suitable carriers include, but are not limited to, physiologic saline, phosphate buffered saline, phosphate buffered saline glucose and buffered saline. Alternatively the immunoglobulin may be lyophilised (freeze dried) and reconstituted for use when needed by the addition of an aqueous buffered solution as described above. Routes of administration are routinely parenteral, including intravenous, intramuscular, subcutaneous and intraperitoneal injection or delivery. The chelating agent may be incorporated into any type of immunoglobulin formulation intended either for storage and distribution or ultimate use. The pharmaceutical formulation will generally contain, or in the case of a lyophilised preparation will be reconstituted to contain, an effective therapeutic dose of the immunoglobulin per unit dose. the case of the humanised antibody CAMPATH-1H, liquid formulations or reconstituted lyophilised formulations preferably contain 0.5 to 20 mg/ml of the antibody, preferably 2 mg/ml or 10 mg/ml.

The invention is illustrated by the following examples:

EXAMPLE 1

The effect of various additives on the stability of a recombinant antibody was studied at 37° C. The antibody was CAMPATH 1H, a humanised antibody against the CDw52 antigen (Riechmann et al, Nature, 322, 323–327 (1988)), which had been produced by expression in a recombinant CHO cell line transformed with DNA encoding the heavy and light chains of the antibody molecule. The antibody was extracted from the cell culture medium and purified and was then stored as a solution (1 mg/ml) in phosphate buffered saline at +4° C.

Vials containing 0.5 ml of the solution of CAMPATH 1H referred to above together with the additive specified were incubated at +37° C. for 4 weeks under sterile conditions. At the end of this period the samples were analysed by size exclusion HPLC, the stability of the sample being assessed by the extent of the formation of "peak C" (a peak formed by the major degradation product of the antibody which has a molecular weight of about 50 K) based on the total eluted protein. The results are set out in the following Table 1.

TABLE 1

| ADDITIVE | % PEAK C |
| --- | --- |
| None | 12% |
| None (storage at +4° C.) | 2% |
| $Cu^{++}$ (10 ppm) | 28% |
| EDTA (2 mM) | <1% |
| 1,10-phenanthroline (10 mM) | 3% |

The copper was added as $CuCl_2.2H_2O$ and the 1,10-phenanthroline as a solution in water containing 2% (v/v) ethanol.

These results demonstrate that copper enhances the degree of degradation of the antibody relative to the control. The addition of EDTA virtually eliminates degradation whilst the other metal ion chelator 1,10-phenanthroline reduces degradation to a considerable extent.

EXAMPLE 2

This example also used CAMPATH 1H produced in CHO cells of the type referred to in Example 1 (11.3 mg/ml in phosphate buffered saline) and the batch having been measured as containing 0.04 µg $Cu^{2+}$/ml. In this and following examples, the copper content of antibody samples was measured by atomic absorption spectroscopy using a Philips PU9400X atomic absorption spectrophotometer. The detection limit of this method was about 0.03 µg Cu/ml so that samples stated to have "no detectable copper" contain less than 0.03 µg Cu/ml. Samples of this Campath 1H were diluted to 1 mg/ml in phosphate buffered saline and dialysed exhaustively versus 0.2 M sodium phosphate buffer at pH 6.0, pH 6.4 and pH 6.8. CAMPATH 1H previously having been determined to be most stable against degradation by heat at about pH 6. The following was added to 300 µl samples at each pH:

(i) 30 µl 10 mM $CuCl_2.2H_2O$ in water;

(ii) 30 µl 10 mM EDTA in water;

(iii) 30 µl buffer;

and the samples incubated at 62° C. for 24 hours. 50 µl aliquots were analysed as described in Example 1 with degradation being assessed by size exclusion chromatography and measured as the extent of formation of "Peak C" based on the total eluted protein.

The results for % Peak C are given in Table 2 below:

TABLE 2

| | % Peak C | | |
| --- | --- | --- | --- |
| pH | Cu | EDTA | Buffer |
| 6.0 | 1.75 | 0.38 | 0.69 |
| 6.4 | 2.94 | 0.34 | 0.72 |
| 6.8 | 5.31 | 0.51 | 1.12 |

The results indicate that as pH increases, the effect of copper on the degradation of CAMPATH 1H increases. In the absence of added copper an increase in % Peak C is also seen with increasing pH. In the presence of EDTA the degradation of CAMPATH 1H is suppressed.

EXAMPLE 3

This example used two different batches of CAMPATH 1H produced in CHO cells of the type referred to in Example 1 (10 mg/ml in phosphate buffered saline): Batch 1 contained no detectable $Cu^{2+}$ as determined by atomic absorption spectroscopy and Batch 2 contained 0.04 µg $Cu^{2+}$/ml. Samples of both batches were diluted to 1 mg/ml in phosphate buffered saline and dialysed extensively for 24 hours at +4° C. against 50 mM ammonium hydrogen carbonate and 1 mM EDTA was added to the Batch 2 to eliminate any effect of the copper. 200 µl aliquots of both batches were incubated for 24 hours at 4°, 10°, 20°, 30°, 40°, 50° and 62° C. and degradation was assessed as described in Example 1 by size exclusion chromatography and measured as the extent of formation of "Peak C" based on the total eluted protein.

The results for % Peak C are given in Table 3 below:

TABLE 3

| | % Peak C | |
| --- | --- | --- |
| Temperature | Batch 1 | Batch 2 + EDTA |
| 4° C. | 0 | 0 |
| 10° C. | 0 | 0 |
| 20° C. | 0 | 0 |
| 30° C. | 0.47 | 0 |
| 40° C. | 2.71 | 0 |
| 50° C. | 60.1 | 0 |
| 62° C. | 72.36 | 1.12 |

Although no detectable $Cu^{2+}$ was found in Batch 1, some degradation was apparent on incubation at 30° and 40° C. with extensive degradation at 50° and 62° C. In the case of Batch 2 which contained detectable $Cu^{2+}$, minimal degradation was seen even at elevated temperature in the presence of EDTA. These results suggest the possibility that subdetectable levels of $Cu^{2+}$ may accelerate the degradation of CAMPATH 1H.

EXAMPLE 4

The results of Example 1 were confirmed by a timed incubation at 62° C. over a period of 24 hours using the same CAMPATH 1H antibody produced in CHO cells. The batch used was determined to contain 0.03 µg $Cu^{2+}$/ml by atomic absorption spectroscopy and 3 ml of this batch containing 3.7 mg/ml CAMPATH 1H in phosphate buffered saline was dialysed at +4° C. for 24 hours against 3×2 litres 50 mM ammonium hydrogen carbonate. 100 µl aliquots were incubated at 62° C. with the following additions:

(i) 5 µl 0.01 M EDTA in water+10 µl 0.1 M $CuCl_2.2H_2O$ in water;

(ii) 5 µl 0.01 M EDTA in water;

(iii) none.

The amount of EDTA added should have been sufficient to chelate any residual transition metal ions in the antibody but not sufficient to chelate the copper which is added in Sample (i).

50 µl samples were withdrawn for analysis at the following times: 0, 1, 2, 3, 4, 5 and 24 hours. The samples were analysed as in Example 1 by size exclusion HPLC with the extent of formation of Peak C again being taken as a measure of the extent to which the antibody had been degraded. The results are shown in the following Table 4:

TABLE 4

| Time hours | % Peak C | | |
|---|---|---|---|
| | EDTA + Cu | EDTA | None |
| 0 | 0 | 0 | 0 |
| 1 | 2.49 | 0 | 1.13 |
| 2 | 9.20 | 0 | 1.82 |
| 3 | 39.24 | 0 | 3.27 |
| 4 | 44.83 | 0 | 5.13 |
| 5 | 49.42 | 0 | 6.89 |
| 24 | 100 | 2.25 | 22.12 |

EXAMPLE 5

This example also used CAMPATH 1H produced in CHO cells of the type referred to in Example 1 (10.0 mg/ml in phosphate buffered saline) and the batch having no detectable copper as measured by atomic absorption spectroscopy. A sample of this CAMPATH 1H was dialysed at +4° C. versus 50 mM ammonium hydrogen carbonate and 100 μl aliquots were incubated at 62° C. for 24 hours with 10 μl of increasing concentrations of $CuCl_2.2H_2O$ in water. The samples were analysed as in Example 1 by size exclusion HPLC with the extent of formation of "Peak C" again being taken as a measure of the extent to which the antibody had been degraded. The results are shown in the following Table 5:

TABLE 5

| nMoles Cu per nMole CAMPATH 1H | % Peak C |
|---|---|
| 0 | 1.61 |
| 0.018 | 8.09 |
| 0.037 | 11.41 |
| 0.074 | 13.61 |
| 0.145 | 17.59 |
| 0.293 | 22.84 |

The extent of degradation was found to increase with increasing molar ratio of $Cu^{2+}$/CAMPATH 1H. At ratios above 0.3 (data not shown), aggregation was seen with lower recovery of total protein.

EXAMPLE 6

This example also used CAMPATH 1H produced in CHO cells of the type referred to in Example 1 (1.0 mg/ml in phosphate buffered saline), the batch having been found to contain 0.19 μg $Cu^{2+}$/ml as measured by atomic absorption spectroscopy. The sample thus had a high copper content (copper/CAMPATH 1H molar ratio 449 pMol $Cu^{2+}$/nMol CAMPATH 1H) and early stability studies showed that this batch was subject to substantial degradation on storage at 37° C.

The effect of incubation of this sample for up to four weeks at 37° C. with and without the presence of 2 mM EDTA is shown below in Table 6. The samples were analysed as in Example 1 by size exclusion HPLC with the extent of formation of "Peak C" again being taken as a measure of the extent to which the antibody had been degraded.

TABLE 6

| Time (weeks) | % Peak C | |
|---|---|---|
| | 2 mM EDTA | No EDTA |
| 1 | 0.72 | 2.86 |
| 2 | 1.26 | 6.59 |
| 3 | 1.24 | 9.24 |
| 4 | 1.44 | 10.18 |
| 4 at +4° C. | 0.95 | 1.02 |

2 mM EDTA substantially decreases the decomposition of the CAMPATH 1H but does not totally inhibit it.

A sample of the same Campath 1H was dialysed at +4° C. versus 50 mM ammonium hydrogen carbonate and 100 μl aliquots were incubated at 62° C. for 24 hours with varying concentrations of EDTA. Again the samples were analysed as in Example 1 by size exclusion HPLC with the extent of formation of "Peak C" being taken as a measure of the extent to which the antibody had been degraded. The results of two separate experiments are shown in Tables 7 and 8 below:

TABLE 7

| mM EDTA | % Peak C |
|---|---|
| 0 | 6.86 |
| 0.1 | 1.03 |
| 1 | 1.38 |
| 2 | 1.12 |
| 3 | 1.26 |
| 4 | 1.04 |
| 10 | 1.20 |

TABLE 8

| mM EDTA | % Peak C |
|---|---|
| 0 | 7.47 |
| 0.0001 | 8.43 |
| 0.001 | 7.28 |
| 0.01 | 1.83 |
| 0.04 | 1.68 |
| 0.1 | 1.63 |

These results show that as little as 0.01 mM EDTA effectively inhibits decomposition of CAMPATH 1H.

EXAMPLE 7

The effect of $Cu^{2+}$ and of EDTA on the decomposition of various antibodies is shown in Table 9 below. All samples were incubated at 4° C. and at 62° C. for 24 hours in the absence of any additives and at 62° C. for 24 hours in the presence of either $Cu^{2+}$(1 mM $CuCl_2.2H_2O$+0.5 mM EDTA) or EDTA (1 mM EDTA).

TABLE 9

| Antibody | % Peak C | | | |
|---|---|---|---|---|
| | 4° C. No EDTA | 62° C. No EDTA | 62° C. + $Cu^{2+}$ | 62° C. + EDTA |
| IgG1 | 0.54 | 1.58 | 5.59 | 1.1 |
| C1H | 0 | 2.49 | 27.98 | 0 |
| CD4 | 0.4 | 1.91 | 21.52 | 1.84 |
| IgG2 | 0 | 1.81 | 3.77 | 0 |

TABLE 9-continued

|  | % Peak C | | | |
| --- | --- | --- | --- | --- |
| Antibody | 4° C. No EDTA | 62° C. No EDTA | 62° C. + $Cu^{2+}$ | 62° C. + EDTA |

IgG1 = mouse monoclonal $IgG_1$ antibody, 1 mg/ml in phosphate buffered saline;
C1H = CAMPATH 1H of the type described in Example 1, 1 mg/ml in phosphate buffered saline;
CD4 = Humanised anti-CD4 monoclonal antibody having the same framework region as CAMPATH 1H and produced in CHO cells, 1 mg/ml in phosphate buffered saline;
IgG2 = Mouse $IgG_2$ monoclonal antibody I-4139 commercially from Sigma, supplied lyophilised from phosphate buffer and redissolved with water to 1 mg/ml.

All samples show little or no decomposition at 4° C. whereas there is some decomposition at 62° C. which is increased by varying degrees by the presence of copper. Decomposition at 62° C. is suppressed by EDTA.

EXAMPLE 8

A comparison between the effect of 2 mM EDTA in phosphate buffered saline (pH 7.2) and 50 mM citrate (pH 6.0) on the stability of Campath-1H was carried out at various levels of copper. Campath-1H produced in CHO cells of the type referred to in Example 1, the batch having no detectable copper as measured by atomic absorption spectroscopy, was diluted 1 in 10 by volume with Phosphate buffered saline. 1 ml aliquots were dialysed against 1 litre of the following buffers:

(i) phosphate buffered saline, pH 7.2;

(ii) 2 mM EDTA in phosphate buffered saline, pH 7.2;

(iii) 50 mM sodium citrate, pH 6.0.

Dialysis was carried out at 4° C. with three changes over 16 hours. Protein concentration was then determined for the three samples by scanning between 340 and 200 nm using a buffer blank and taking the extinction coefficient $A_{280}$ (0.1%) as 1.32. Protein concentrations of:

(i) 1.32 mg/ml (ii) 1.20 mg/ml (iii) 1.27 mg/ml were determined.

200 µl aliquots of the antibody in the above buffers were then incubated with increasing concentrations of $CuCl_2.2H_2O$ (up to 20 mM) at 62° C. for 24 hours (62° C. being the optimal temperature for copper-induced cleavage of Campath-1H.) Samples (50 µl aliquots) were then analysed by size exclusion HPLC in the manner described in Example 1 and the various fractions integrated by cutting and weighing chromatograms of the $A_{280}$—absorbing peaks eluted from the column. In this case, results were recorded as % "peak B" (whole Campath-1H).

The results are set out in the following Table 10.

TABLE 10

| Added | % Peak B | | |
| --- | --- | --- | --- |
| Cu (mM) | PBS only | PBS + 2 mM EDTA | 50 mM Citrate |
| 0 | 42.92 | 100 | 100 |
| 1 | 21.47 | 98.95 | 94.71 |
| 2.5 | 18.72 | 36.96 | 94.66 |
| 5.0 | 0 | 0 | 93.43 |
| 7.5 | 0 | 0 | 92.82 |
| 10 | 0 | 0 | 92.57 |

TABLE 10-continued

| Added | % Peak B | | |
| --- | --- | --- | --- |
| Cu (mM) | PBS only | PBS + 2 mM EDTA | 50 mM Citrate |
| 12.5 | 0 | 0 | 84.85 |
| 15 | 0 | 0 | 32.53 |
| 20 | 0 | 0 | 15.48 |

Cleavage Campath-1H in phosphate buffered saline alone at pH 7.2 is relatively rapid on incubation for 24 hours at 62° C. even in the absence of added copper. In phosphate buffered saline plus 2 mM EDTA, pH 7.2, cleavage is induced when greater than 1 mM—copper is added. In 50 mM—citrate, pH 6.0, cleavage takes place when copper in excess of 10 mM is added.

EXAMPLE 9

A similar experiment to Example 8 also investigated the effece of varying the pH. Campath-1H produced in CHO cells of the type referred to in Example 1 in phosphate buffered saline, the batch having no detectable copper as measured by atomic absorption spectroscopy, was diluted 1:20 in phosphate buffered saline pH 7.2. Protein concentration was then determined as described in Example 8 and the samples diluted to a protein concentration of 2 mg/ml with phosphate buffered saline pH 7.2 or phosphate buffered saline pH 6.0 and the pH was checked. Either 4 µl 0.1 M—trisodium citrate, pH 7.0 or 4 µl 0.1 M-EDTA, pH 7.0 was added to 200 µl aliquots of each of the Campath-1H samples (2 mg/ml in phosphate buffered saline either pH 7.2 or pH 6.0) to give a final concentration of about 2 mM with respect to citrate of EDTA. Copper was added up to 3 mM as 0 to 6 µl aliquots of 0.1 M $CuCl_2.2_2O$ per 200 µl Campath-1H (2 mg/ml) sample. 4 µl water was added to samples without copper. Samples were incubated at 62° C. for 24 hours, centrifuged to remove any precipitated material and 50 µl aliquots analysed by size exclusion HPLC in the manner described in Example 8. Results, recorded as % "peak B" (whole Campath-1H) are set out in the following Table 11.

TABLE 11

| Added | % Peak B | | | | | |
| --- | --- | --- | --- | --- | --- | --- |
| Cu | PBS only | | PBS + 2 mM EDTA | | PBS + 2 Mm CIT | |
| (mM) | pH 7.2 | pH 6.0 | pH 7.2 | pH 6.0 | pH 7.2 | pH 6.0 |
| 0 | 93.54 | 95.29 | 91.41 | 92.91 | 93.17 | 89.25 |
| 0.5 | 3.24 | 38.46 | 92.86 | 94.87 | 64.81 | 86.63 |
| 1.0 | 17.27 | 12.89 | 94.47 | 93.56 | 66.77 | 84.96 |
| 2.0 | 6.5 | 0 | 95.14 | 13 | 18.36 | 0.74 |
| 2.5 | 25 | 0 | 12.92 | 0 | 38.41 | 0.8 |
| 3.0 | 15.44 | 0 | 13.2 | 0 | 37.5 | 0.93 |

The above table shows the approximate stoichiometry of binding of $Cu^{2+}$ by 2 mM-EDTA and 2 mM-citrate and the contributory effect of pH. 2 mM-EDTA in phosphate buffered saline, pH 7.2, is the most effective in suppressing copper induced cleavage of Campath-1H. An approximate 1:1 stoichiometry of binding is indicated at pH 7.2. Copper concentrations in excess of 2 mM cause cleavage of Campeth-1H in 2 mM EDTA.

We claim:

1. A method of making a stabilized $IgG_1$ composition comprising adding to a starting composition comprising:
   i) $IgG_1$ and
   ii) copper ions in an amount sufficient to degrade said $IgG_1$, an amount of a chelator of copper ions sufficient to stabilize said $IgG_1$ against copper ion-mediated degradation, so that said stabilization $IgG_1$ composition is made.

2. A method in accordance with claim 1, wherein the chelator of copper ions is ethylenediamine tetracetic acid.

3. A method in accordance with claim 1, wherein the chelator of copper ions is citrate ion.

4. A method in accordance with claim 2 or 3, wherein the antibody is a recombinant CDR-grafted antibody against the CDw52 antigen.

5. A method in accordance with claim 1, 2 or 3, wherein the antibody is CAMPATH-1H.

* * * * *

UNITED STATES PATENT AND TRADEMARK OFFICE

CERTIFICATE OF CORRECTION

PATENT NO.    : 5,792,838
DATED         : August 11, 1998
INVENTOR(S)   : SMITH et al It is certified that error appears in the above-identified patent and that said letters patent is hereby corrected as shown below:

Face Page, item [63], after "1994" insert --, now USP 5,654,403, which is a 371 of PCT/GB/01970, Oct. 27, 1992--.

Column 1, line 5, after "1994" insert --, now USP 5,654,403, which is a 371 of PCT/GB92/01970, filed Oct. 27, 1992--.

Column 11, line 8, change "stabilization" to --stabilized--.

Signed and Sealed this

Fifteenth Day of May, 2001

*Attest:*

NICHOLAS P. GODICI

*Attesting Officer*     *Acting Director of the United States Patent and Trademark Office*